(12) United States Patent
Hu et al.

(10) Patent No.: US 9,733,175 B2
(45) Date of Patent: Aug. 15, 2017

(54) FULL-AUTOMATIC ERYTHROCYTE SEDIMENTATION RATE ANALYSIS METER AND DETECTING METHOD THEREOF

(71) Applicant: SHENZHEN YHLO BIOTECH CO., LTD, Shenzhen (CN)

(72) Inventors: Kunhui Hu, Shenzhen (CN); Hui Yang, Shenzhen (CN); Qingbo Liu, Shenzhen (CN); Lin He, Shenzhen (CN)

(73) Assignee: SHENZHEN YHLO BIOTECH CO., LTD., Shenzhen (CN)

( * ) Notice: Subject to any disclaimer, the term of this patent is extended or adjusted under 35 U.S.C. 154(b) by 358 days.

(21) Appl. No.: 14/434,360

(22) PCT Filed: Jun. 19, 2013

(86) PCT No.: PCT/CN2013/077433
§ 371 (c)(1),
(2) Date: Apr. 8, 2015

(87) PCT Pub. No.: WO2014/201626
PCT Pub. Date: Dec. 24, 2014

(65) Prior Publication Data
US 2015/0268148 A1    Sep. 24, 2015

(51) Int. Cl.
*G01N 15/05* (2006.01)
*G01N 33/49* (2006.01)
(Continued)

(52) U.S. Cl.
CPC ............ *G01N 15/05* (2013.01); *B01F 9/002* (2013.01); *B01F 13/0098* (2013.01); *G01N 1/38* (2013.01);
(Continued)

(58) Field of Classification Search
CPC ........ G01N 15/05; G01N 1/38; G01N 33/491; G01N 2015/0073; G01N 2035/00524;
(Continued)

(56) References Cited

U.S. PATENT DOCUMENTS 5,284,623 A * 2/1994 Yamori .................. B01L 99/00
                                                      211/74
5,367,157 A    11/1994 Nilsson et al.
(Continued)

FOREIGN PATENT DOCUMENTS

CN    2062448    9/1990
CN    2258617    7/1997
(Continued)

*Primary Examiner* — David Porta
*Assistant Examiner* — Gisselle Gutierrez
(74) *Attorney, Agent, or Firm* — Hamre, Schumann, Mueller & Larson, P.C.

(57) ABSTRACT

The invention provides a full-automatic erythrocyte sedimentation rate analyzer, which comprises a base as well as a blending device and a detecting device mounted on the base, wherein the blending device comprises a sample rack, a sample rack bracket and a rotating device; the sample rack bracket is arranged on the base, and is connected to the sample rack through a rotating shaft; more than one test tube rack is arranged on the sample rack; the rotating device is connected to the rotating shaft, and drives the rotating shaft to rotationally drive the sample rack to turn over up and down; a plurality of holes are arranged in each test tube rack; a fixing device is arranged in the hole, and used for placing and fixing a closed container containing samples; the detecting device comprises a guide device, a driving device, infrared transmitting and receiving devices having the same quantity as that of the test tube racks, and a mounting rack; the driving device drives the mounting rack to move up and down along the guide device; the mounting rack drives the infrared transmitting and receiving devices to move; the
(Continued)

closed containers containing the samples are located on moving paths of the infrared transmitting and receiving devices; and infrared rays penetrate through the closed containers to realize detecting.

6 Claims, 6 Drawing Sheets

(51) Int. Cl.
*B01F 9/00* (2006.01)
*B01F 13/00* (2006.01)
*G01N 1/38* (2006.01)
*G01N 15/04* (2006.01)
*G01N 35/00* (2006.01)
*G01N 15/00* (2006.01)

(52) U.S. Cl.
CPC ... *G01N 33/491* (2013.01); *G01N 2015/0073* (2013.01); *G01N 2015/045* (2013.01); *G01N 2035/00524* (2013.01)

(58) Field of Classification Search
CPC  G01N 2015/045; B01F 13/0098; B01F 9/002
USPC ........................................................ 250/338.1
See application file for complete search history.

(56) References Cited

U.S. PATENT DOCUMENTS

2006/0286619 A1* 12/2006  Ricci ..................... B01L 9/06
                                                                435/13
2007/0231208 A1* 10/2007  Tanaka ............ G01N 35/00603
                                                                422/67

FOREIGN PATENT DOCUMENTS

| | | | | |
|---|---|---|---|---|
| CN | 2802499 | * | 8/2006 | ............. G01N 15/05 |
| JP | 6439552 | | 2/1989 | |
| SE | WO 9105996 A1 | * | 5/1991 | ............. G01N 15/05 |

* cited by examiner

FULL-AUTOMATIC ERYTHROCYTE SEDIMENTATION RATE ANALYSIS METER AND DETECTING METHOD THEREOF

FIELD OF THE INVENTION

The present invention relates to an instrument for full-automatic analysis of natural erythrocyte sedimentation in a blood sample and a detecting method thereof, which belongs to the technical field of medical detection facilities.

BACKGROUND OF THE INVENTION

Erythrocyte sedimentation rate (ESR) is a sedimentation velocity of the erythrocyte in a unit time, the value of which is affected by the size, shape, quantity of the erythrocyte and other plasma components. The ESR is used as the prognosis and treatment index of some diseases like rheumatic fever and tuberculosis, and may also be used as a reference index for identifying some functional diseases and organic diseases.

The ESR is mostly measured by using a Westergren method blood sedimentation tube at present. The Westergren method blood sedimentation tube is a glass tube with scales. A blood sample uniformly mixed with anticoagulant according to a certain rate is sucked in the Westergren method blood sedimentation tube, and then the tube is vertically placed on a blood sedimentation rack; the initial height scale of sedimentation of the erythrocyte is recorded. The blood sample is naturally sedimentated for 60 min and the sedimentation scale is recorded, thus obtaining the nature sedimentation height of the erythrocyte within 1 hour, which is namely a blood sedimentation result required by the clinic. However, the Westergren method has multiple disadvantages during operation: 1, a test operator is directly contacted with the blood sample, which has a certain potential hazard to the operator; 2, the sedimentation scale is directly interpreted by human eyes, which causes an artificial difference; 3, the 60 minute sedimentation time is overlong, which causes a lower efficiency; and 4, adopting the manner of manual blending requires long term shaking by hand and also causes a poor blending effect.

An ESR detection facility which can obtain the detection result in a very short time, performs a sample enclosed manner, has accurate results and has excellent dependence with the Westergren method is urgently needed clinically.

SUMMARY OF THE INVENTION

The present invention aims at solving the technical problem of: providing an automatic ESR tester and a detecting method thereof, which can overcome the defects of complex operating, long detecting time and direct contact with the blood sample of the traditional Westergren manual method while detecting the ESR as well as the problems that some existing blood sedimentation meters measure inaccurately and require a special blood sedimentation tube.

One objective of the present invention is to provide a full-automatic erythrocyte sedimentation rate analysis meter, the technical solution of which is realized as follows.

The full-automatic erythrocyte sedimentation rate analyzer, which comprises a base as well as a blending device and a detecting device mounted on the base, wherein the blending device comprises a sample rack, a sample rack bracket and a rotating device. The sample rack bracket is arranged on the base and is and connected to the sample rack through a rotating shaft. More than one test tube rack is arranged on the sample rack. The rotating device is connected to the rotating shaft, and drives the rotating shaft to rotationally drive the sample rack to turn over up and down. A plurality of holes are arranged in each test tube rack. A fixing device is arranged in the hole, and used for placing and fixing a closed container containing samples. The detecting device comprises a guide device, a driving device, infrared transmitting and receiving devices having the same quantity as that of the test tube racks, and a mounting rack for mounting and fixing the infrared transmitting and receiving devices. The driving device drives the mounting rack to move up and down along the guide device. The mounting rack drives the infrared transmitting and receiving devices to move. The closed containers containing the samples are located on moving paths of the infrared transmitting and receiving devices; and infrared rays penetrate through the closed containers to realize detecting.

Further, the rotating device comprises an upper gear arranged on the rotating shaft and coaxial with the rotating shaft. A lower gear is arranged on the base; a first driving band is sleeved between the upper gear and the lower gear; and the lower gear is driven by a first motor arranged on the base.

Further, the first driving band drives the rotating shaft to rotate by 180 degrees so as to drive the sample rack to turn by 180 degrees and realize sufficient blending of the samples.

Further, the guide device is a guide rail fixing seat arranged on the base and vertical to the base. The driving device comprises an upper connecting body and a lower connecting body mounted with a second driving band and provided with a gear. A guide rail is arranged on the guide rail fixing seat. A gliding block which may glide along the guide rail is mounted on the guide rail. The mounting rack is fixed on the gliding block. The lower connecting body is driven to rotate by a second motor; and the second driving band drives the gliding block to move up and down along the guide rail.

Further, the infrared transmitting and receiving device comprises a transmitting plate mounted with a plurality of infrared transmitting tubes and a receiving plate mounted with a plurality of infrared receiving tubes. The infrared transmitting tubes and the infrared receiving tubes are corresponding one by one. The transmitting plate and the receiving plate are spaced by a certain distance that allows the closed container containing the samples to penetrate through.

Further, the fixing device is an elastic clamping sheet arranged in the hole and used for clamping the closed container containing the samples.

Further, the full-automatic erythrocyte sedimentation rate analysis meter further comprises an indicator light arranged at the top end of the analysis meter and used for indicating the working state of the analysis meter.

Further, the full-automatic erythrocyte sedimentation rate analysis meter further comprises a towline arranged on the analysis meter and used for placing various connecting wires.

Another objective of the present invention is to provide a detecting method using the foregoing analysis meter, which specifically comprises the following steps of:
1. Starting up, wherein an analysis meter performs self-check;
2. Scanning a bar-code of a blood collection tube which is filled with a blood sample, is sealed and contains anticoagulant, and placing the blood collection tube in the hole of the sample rack;

3. Clicking "Operate" on a software operating interface to enter a detection program;
4. Starting a blending program to rotate the sample rack by 180 degrees, wherein the sample rack is still after the blending is finished;
5. After the blending is finished, automatically scanning and detecting, by the detecting device in the analysis meter, the blood collection tube, and recording information at a zero hour of sedimentation;
6. Scanning the test tube for once in every 10 s and lasting for 20 min for each time (namely scanning for 120 times in total);
7. Recording in real time, by a data collection module, the sedimentation information of the erythrocytes in the test tube in every 10 s, and storing the information in a corresponding storage device;
8. Calculating the result according to a storage formula $ESR=B*SB_{lopB}+C*LB_{initB}+D*Taggr$ in the analysis meter, and obtaining a dynamic curve, wherein the ESR is concerned with the initial height ($LB_{initB}$), the zero hour of sedimentation (Taggr) of the erythrocytes as well as the maximum sedimentation rate ($SB_{lopB}$) during a sedimentation process and the finial height ($TB_{finB}$) of the erythrocyte; for blood samples of different heights, the blood sedimentation value ESR may be represented by a formula $ESR=B*SB_{lopB}+C*LB_{initB}D*Taggr$ (wherein, B, C and D are coefficients that can be obtained by using a linear regression method); and
9. Transmitting and printing a result report.

The present invention is used for collecting a closed container for containing blood samples, wherein the closed container is namely a blood collection tube added with anticoagulant and used for sample collection for cell counting and detecting. The samples may be residual blood samples after the cell counting, and the tube is not needed to be opened to add any other anticoagulant.

The analysis meter and the method according to the present invention, by utilizing the sedimentation rules of the blood sample in the blood collection tube, and after automatically blending the samples, can quickly and accurately read the sedimentation information of the erythrocyte, reduce the labour intensity of the operating personnel, avoid the operating personnel from being directly contacted with the blood sample, and has the advantages of convenient and simple operation, quick measurement, reliable and accurate result, and very good dependence with the Westergren method.

Wherein, 1 refers to a base, 21 refers to a sample rack bracket, 22 refers to a test tube rack, 220 refers to a hole, 23 refers to a closed container, 24 refers to a lower gear, 25 refers to an upper gear, 26 refers to a first driving band, 27 refers to a rotating shaft, 28 refers to a sample rack, 3 refers to a mounting rack, 41 refers to a transmitting plate, 42 refers to a receiving plate, 410 refers to an infrared transmitting tube, 420 refers to an infrared receiving tube, 51 refers to a guide plate, 52 refers to a guide rail, 53 refers to an upper connecting body, 54 refers to a lower connecting body, 55 refers to a second driving band, 56 refers to a gliding block, 61 refers to an indicator light, 62 refers to a mainboard, 63 refers to a towline, 64 refers to a switch baffle, 65 refers to a first motor, 66 refers to a second motor, 67 refers to a power panel, 68 refers to a first switch power supply, and 69 refers to a switch power supply.

DETAILED DESCRIPTION OF THE EMBODIMENTS

To make the public better understand the contents, the structure of the present invention is described in a nonrestrictive manner hereinafter with reference to the accompanying drawings.

Figure 1:
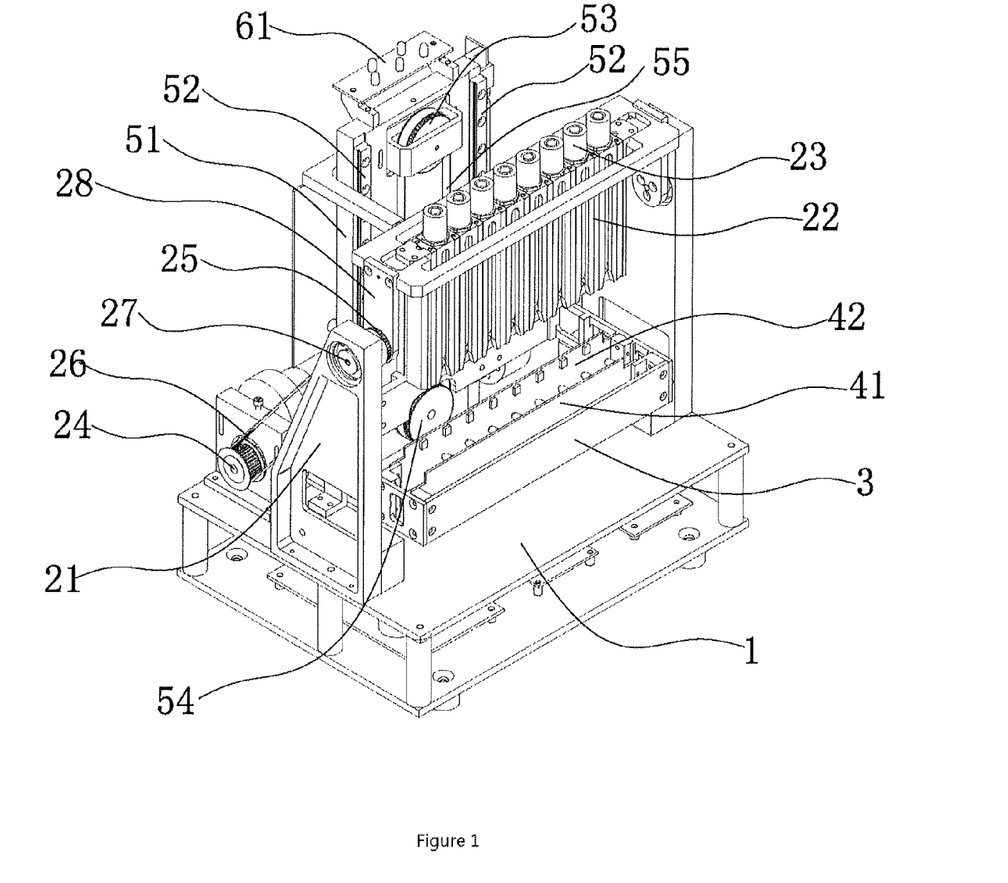
FIGS. 1-3 are axial views of a first embodiment of the present invention from different angles.
Figure 2:
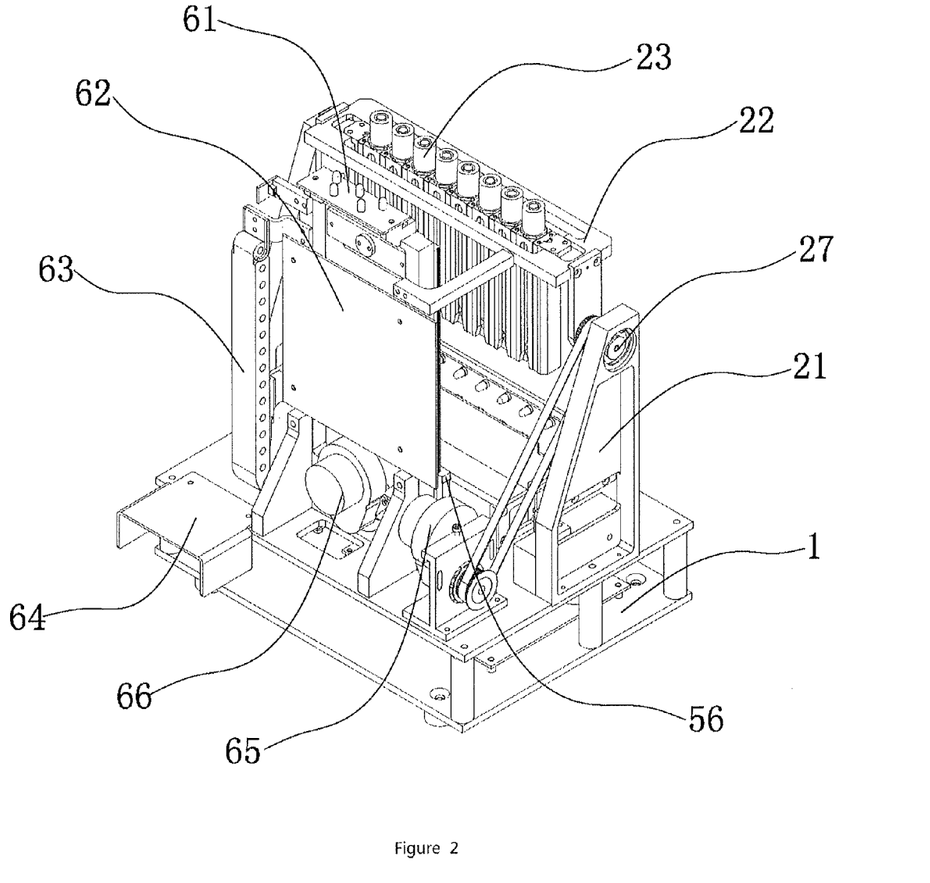
Figure 3:
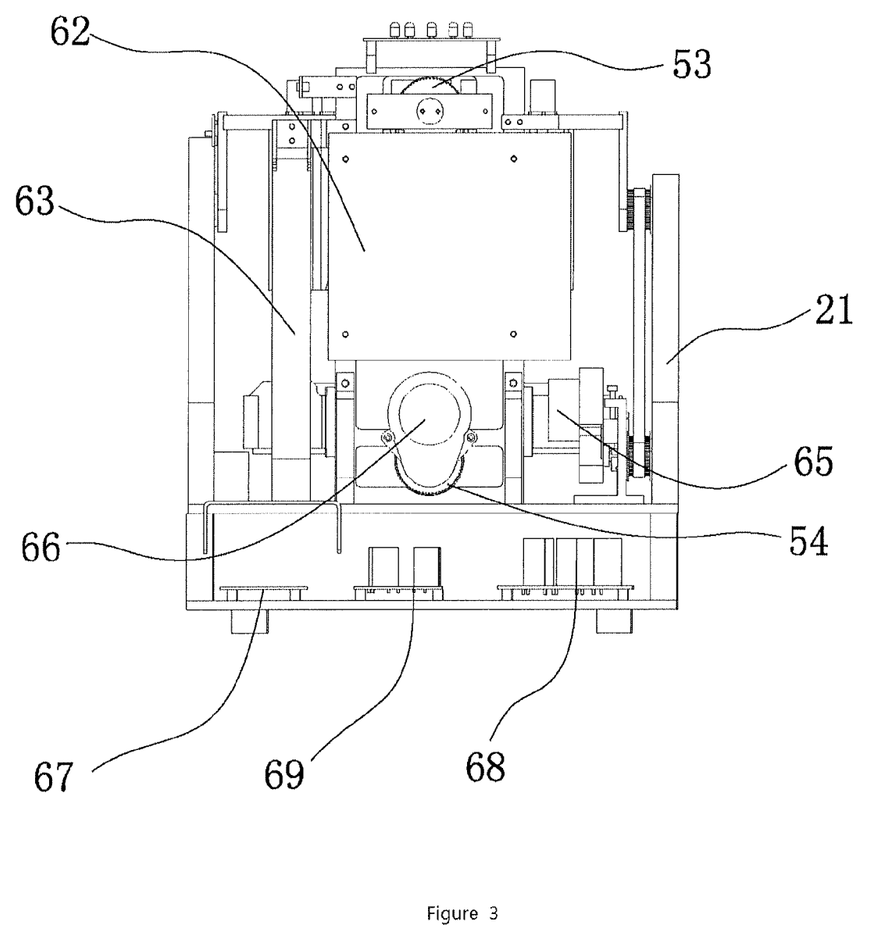
Figure 4:
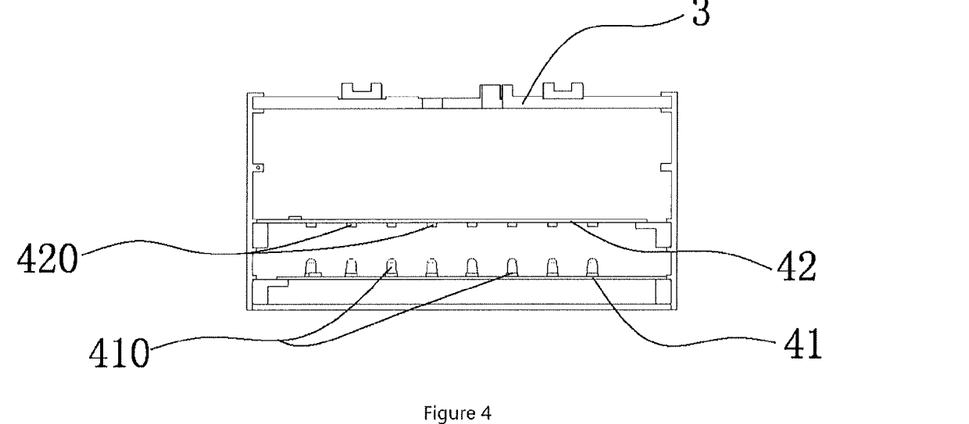
FIGS. 4-5 are schematic views of a mounting rack and an infrared transmitting and receiving device of the first embodiment of the present invention.
Figure 5:
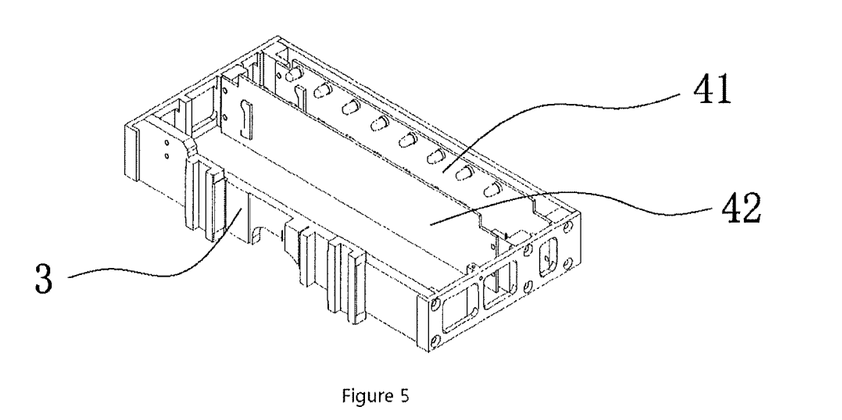
Figure 6:
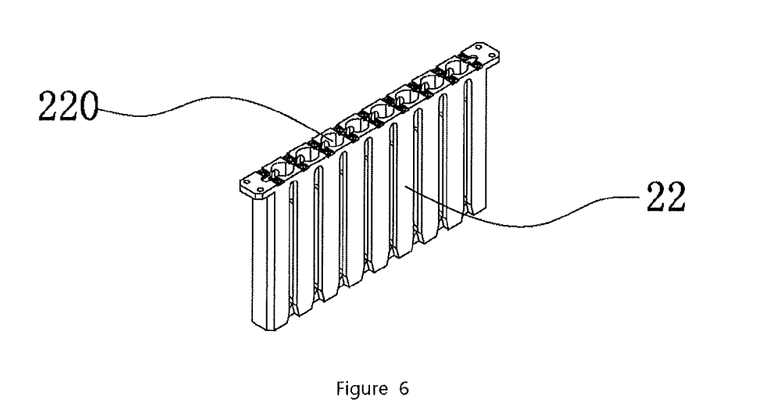
FIG. 6 is a structural schematic view of a test tube rack of the first embodiment of the present invention.

First Embodiment:

As shown in FIGS. 1-3, the full-automatic erythrocyte sedimentation rate analysis meter comprises a base 1 as well as a blending device and a detecting device mounted on the base 1, wherein the blending device comprises a sample rack 28, a sample rack bracket 21 and a rotating device. The sample rack bracket 21 is arranged on the base 1 and is and connected to the sample rack 28 through a rotating shaft 27. A test tube rack 22 is arranged on the sample rack 28. A plurality of holes 220 (see FIG. 6) are arranged on the test tube rack 22. A fixing device is arranged in the hole 220, wherein the fixing device is an elastic clamping sheet used for clamping in the embodiment. The hole 220 is used for placing and fixing a closed container 23 containing samples. The rotating device comprises an upper gear 25 arranged on the rotating shaft 27 and coaxial with the rotating shaft 27. A lower gear 24 is arranged on the base 1; a first driving band 26 is sleeved between the upper gear and the lower gear; and the lower gear 24 is driven by a first motor 65 arranged on the base 1. The first motor 65 is controlled by a first switch power supply 68 arranged on the base 1. The first driving band 26 drives the rotating shaft 27 to rotate by 180 degrees so as to drive the sample rack 28 to turn by 180 degrees and realize sufficient blending of the samples. The detecting device comprises a guide device, a driving device, infrared transmitting and receiving devices having the same quantity as that of the test tube racks, and a mounting rack for mounting and fixing the infrared transmitting and receiving devices. In the embodiment, the guide device is a guide plate 51 arranged on the base 1 and is vertical to the base 1. Two guide rails 52 are arranged on the guide plate 51. Two gliding blocks 56 which may glide along the guide rails 52 are mounted on the guide rails 52. The driving device comprises an upper connecting body 53 and a lower connecting body 54 mounted with a second driving band 55 and provided with a gear. The mounting rack 3 is fixed on the gliding block 56. The lower connecting body 54 is driven to rotate by a second motor 66. The second motor 66 is controlled by a first switch power supply 69 arranged on the base 1. A power panel 67 is also arranged on the base 1. The second driving band 55 drives the gliding block 56 to move up and down along the guide rail 52. As shown in FIGS. 4-5, the infrared transmitting and receiving device having the same quantity as that of the test tube rack 22 is arranged on the mounting rack 3. The infrared transmitting and receiving device comprises a transmitting plate 41 mounted with a plurality of infrared transmitting tube 410 and a receiving plate 42 mounted with a plurality of infrared receiving tube 420. The infrared transmitting tubes 410 and the infrared receiving tubes 420 are corresponding one by one. The transmitting plate 41 and the receiving plate 42 are spaced by a certain distance that allows the closed container 23 containing the samples to penetrate through.

Further, the full-automatic erythrocyte sedimentation rate analysis meter further comprises corresponding electrical equipment, which comprises an indicator light 61 arranged at the top end of the analysis meter and used for indicating the working state of the analysis meter, and further comprises a mainboard 62 arranged at the rack and behind the guide plate 51. The full-automatic erythrocyte sedimentation rate analysis meter further comprises a towline 63 arranged on the analysis meter. The towline 63 is used for placing various connecting wires. A switch baffle 64 is further arranged on the base 1 and a switch is mounted below the switch baffle.

Figure 7:
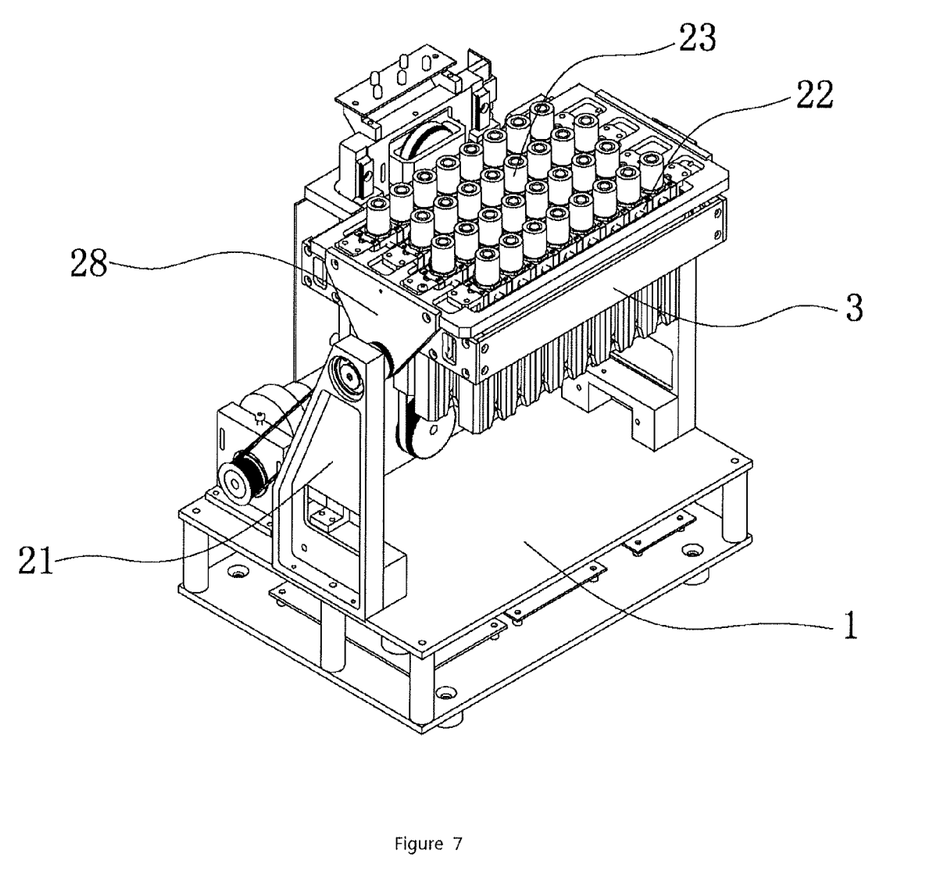
FIG. 7 is a structural view of a second embodiment of the present invention.

Second Embodiment:

As shown in FIG. 7, in the embodiment, a plurality of test tube racks 22 are arranged on the sample rack 28. Accordingly, infrared transmitting and receiving devices having the same quantity as that of the test tube racks 22 are also arranged on the mounting rack 3. The sample rack 28 may be driven by the first motor and the first driving band to rotate by 180 degrees to sufficiently turn and blend the samples. After the samples are completely blended, the mounting rack 3 is driven by the second motor and the second driving band to move up and down, to finish the detecting on the blood sedimentation rate of the sample in the closed container.

To conveniently calculate, store and print the obtained data, a computer is applied in the analysis meter to control the analysis meter. A data collection result is analyzed by the computer, and then is displayed and printed. Moreover, a dynamic curve in the sedimentation process of the erythrocyte may be displayed.

The full-automatic dynamic blood sedimentation analysis meter according to the present invention is a full-automatic dynamic blood sedimentation analysis meter that uses EDTA as a detecting tube, can automatically blend the samples, keeps the samples in the closed container all the time, does not require the operating personnel to be contacted with the samples, does not produce any waste liquor, can reduce the biological hazard to the maximum extent, and the result obtained through the analysis meter has excellent dependence with that of the Westergren blood sedimentation method.

The Westergren blood sedimentation method is a standard method for detecting blood sedimentation recommended by International Committee for Standardization in Hematology (ICSH). A Westergren blood sedimentation tube used is an elongated glass tube as long as 20 cm. The sample needs to be sufficiently blended with a 3.8% sodium citrate solution, and the blended sample is moved in the blood sedimentation tube as long as 20 cm, and is vertically still for 60 min to record the corresponding erythrocyte sedimentation height which is namely the blood sedimentation value. The Westergren method has the disadvantages of complicated operation, mass sample volume, direct contact with blood sample, and long time consumption.

Figure 8:
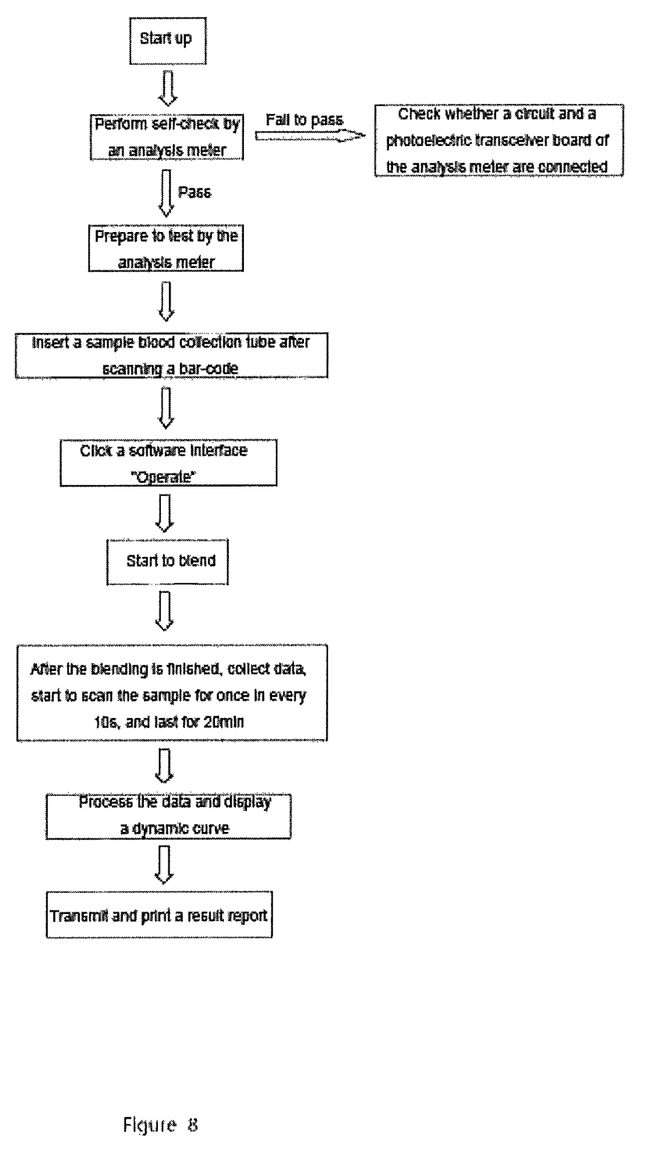
FIG. 8 is a working flow chart of the present invention.

The full-automatic erythrocyte sedimentation rate analysis meter according to the present invention adopts an EDTA blood collection tube as the detecting tube. The EDTA blood collection tubes of various specifications can be adopted. Test can be performed when the minimum blood volume is 1.5 ml. After the anticoagulating whole blood of EDTA is automatically reversed for multiple times and sufficiently blended through the sample rack of the analysis meter, the sample rack is still. The infrared transmitting and receiving device starts to scan up and down along the direction of the test tube. The infrared transmitting and receiving tubes can scan and record the interface height of the erythrocyte after sedimentation. The scanning is carried out for once in every 10 s and each time lasts for 20 min. The analysis meter automatically collects and records the sedimentation result of each scanning and forms the data of the 20 min in a dynamic curve. The analysis meter analyzes the sedimentation rules of the 20 min, and sums up the sedimentation rules as a calculation equation through a large number of experimental data, obtains the blood sedimentation result value of the analysis meter according to the present invention according to the equation, and compares the value with that of the Westergren blood sedimentation method. See FIG. 8 for specific flows.

It should be understood that the drawings included in the foregoing description are not intended to limit the technology. In fact, any improvement made on the full-automatic dynamic blood sedimentation analysis meter with same or similar principles, including equivalent replacement on corresponding element functions as well as improvement on various structure shapes, sizes and materials, shall fall within the technical solution claimed by the present invention.

The invention claimed is:

1. A full-automatic erythrocyte sedimentation rate analysis meter, comprising a base as well as a blending device and a detecting device mounted on the base, characterized in that wherein:

the blending device comprises a sample rack, a sample rack bracket and a rotating device;

the sample rack bracket is arranged on the base, and is connected to the sample rack through a rotating shaft;

more than one test tube rack is arranged on the sample rack; the rotating device is connected to the rotating shaft, and drives the rotating shaft to rotationally drive the sample rack to turn over up and down;

a plurality of holes are arranged in each test tube rack;

a fixing device is arranged in the hole, and used for placing and fixing a closed container containing samples;

the detecting device comprises a guide device, a driving device, infrared transmitting and receiving devices having the same quantity as that of the test tube racks, and a mounting rack for mounting and fixing the infrared transmitting and receiving devices;

the driving device drives the mounting rack to move up and down along the guide device;

the mounting rack drives the infrared transmitting and receiving devices to move; the closed containers containing the samples are located on moving paths of the infrared transmitting and receiving devices; and infrared rays penetrate through the closed containers to realize detecting;

the rotating device comprises an upper gear arranged on the rotating shaft and coaxial with the rotating shaft;

a lower gear is arranged on the base;

a first driving band is sleeved between the upper gear and the lower gear; and the lower gear is driven by a first motor arranged on the base;

the guide device is a guide rail fixing seat arranged on the base and vertical to the base;

the driving device comprises an upper connecting body and a lower connecting body mounted with a second driving band and provided with a gear;

a guide rail is arranged on the guide rail fixing seat;

a gliding block which may glide along the guide rail is mounted on the guide rail; the mounting rack is fixed on the gliding block;

the lower connecting body is driven to rotate by a second motor;

and the second driving band drives the gliding block to move up and down along the guide rail;

the infrared transmitting and receiving device comprises a transmitting plate mounted with a plurality of infrared transmitting tubes and a receiving plate mounted with a plurality of infrared receiving tubes;

the infrared transmitting tubes and the infrared receiving tubes are corresponding one by one;

the transmitting plate and the receiving plate are spaced by a certain distance that allows the closed container containing the samples to penetrate through.

2. The full-automatic erythrocyte sedimentation rate analysis meter according to claim 1, wherein the first driving band drives the rotating shaft to rotate by 180 degrees so as to drive the sample rack to turn by 180 degrees.

3. The full-automatic erythrocyte sedimentation rate analysis meter according to claim 1, wherein the fixing device is an elastic clamping sheet arranged in the hole and used for clamping the closed container containing the samples.

4. The full-automatic erythrocyte sedimentation rate analysis meter according to claim 1, wherein the full-automatic erythrocyte sedimentation rate analysis meter further comprises an indicator light arranged at the top end of the analysis meter and used for indicating the working state of the analysis meter.

5. The full-automatic erythrocyte sedimentation rate analysis meter according to claim 1, wherein the full-automatic erythrocyte sedimentation rate analysis meter further comprises a towline arranged on the analysis meter and used for placing various connecting wires.

6. A detecting method of applying full-automatic erythrocyte sedimentation rate analysis meter according to claim 1, specifically comprises the following steps of:
1) starting up, wherein an analysis meter performs self-check;
2) scanning a bar-code of a blood collection tube which is filled with a blood sample, is sealed and contains anticoagulant, and placing the blood collection tube in the hole of the sample rack;
3) clicking "Operate" on a software operating interface to enter a detection program;
4) starting a blending program to rotate the sample rack by 180 degrees, wherein the sample rack is still after the blending is finished;
5) after the blending is finished, automatically scanning and detecting, by the detecting device in the analysis meter, the blood collection tube, and recording information at a zero hour of sedimentation;
6) scanning the test tube for once in every 10s and lasting for 20 min for each time;
7) recording in real time, by a data collection module, the sedimentation information of the erythrocytes in the test tube in every 10 s, and storing the information in a corresponding storage device;
8) calculating the result according to a storage formula $ESR=B*S_{BBlopBB}+C*L_{BBinitBB}+D*T_{aggr}$ in the analysis meter, and obtaining a dynamic curve, wherein the ESR is concerned with the initial height $L_{BBinitBB}$, the zero hour of sedimentation $T_{aggr}$ of the erythrocytes as well as the maximum sedimentation rate $S_{BBlopBB}$ during a sedimentation process and the finial height $T_{BBfinBB}$ of the erythrocyte; for blood samples of different heights, the blood sedimentation value ESR may be represented by a formula $ESR=B*S_{BBlopBB}+C*L_{BBinitBB}+D*T_{aggr}$; and
9) transmitting and printing a result report.

* * * * *